United States Patent [19]

Luo et al.

[11] Patent Number: 5,072,068

[45] Date of Patent: Dec. 10, 1991

[54] METHOD FOR RETRIEVING STYRENE MONOMER FROM DISCARDED POLYSTYRENE SCRAP THROUGH PYROLTIC REDUCTION

[75] Inventors: Xinmin Luo; Fen Yie; Weiguo Tan, all of Kwangchow, China

[73] Assignee: Guangdong International Economic and Technical Group, China

[21] Appl. No.: 480,992

[22] Filed: Feb. 16, 1990

[30] Foreign Application Priority Data

Feb. 17, 1989 [CN] China .................. 891001122.6

[51] Int. Cl.$^5$ ................................................ C07C 1/00
[52] U.S. Cl. ..................................... 585/241; 585/240
[58] Field of Search .......................................... 585/241

[56] References Cited

U.S. PATENT DOCUMENTS

| | | | |
|---|---|---|---|
| 3,692,858 | 9/1972 | Brewer et al. ................ | 585/241 |
| 3,704,108 | 11/1972 | Alpert ........................... | 585/241 |
| 3,974,206 | 8/1976 | Tetsumi et al. ............... | 585/241 |
| 4,584,421 | 4/1986 | Saito et al. .................... | 585/241 |

FOREIGN PATENT DOCUMENTS 2136437 9/1984 United Kingdom .

*Primary Examiner*—Patrick P. Garvin
*Assistant Examiner*—E. D. Irzinski
*Attorney, Agent, or Firm*—Sughrue, Mion, Zinn Macpeak & Seas

[57] ABSTRACT

The invention concerns a method for retrieving styrene monomer from discarded polystyrene scarp through pyrolytic reduction. The method provided by this invention involves the application of metal oxide catalyst and putting alloy additives on the bottom of a pyrolyzer. When the temperature of the pyrolyzer reaches 250° C., the discarded polystyrene granules 3-5 mm in diameter are continuously fed at a constant rate. At the temperature of 350° C. the gas is introduced. The temperature is kept in a range of 450°-500° C., till a batch polystyrene is completely pyrolyzed. During feeding the polystyrene a reduced pressure distillation is carried out. The yield of a liquid distillate is 90% of the feed stock in weight. The recovery rate of styrene amounts to 70-75%. The present invention provides an effective method for solving environmental pollution caused by discarded polystyrene and for retrieving polystyrene.

8 Claims, No Drawings

METHOD FOR RETRIEVING STYRENE MONOMER FROM DISCARDED POLYSTYRENE SCRAP THROUGH PYROLTIC REDUCTION

The present invention relates to a method for retrieving a useful substance from scraps of synthetic polymeric materials, particularly relates to the method for retrieving styrene monomer from discarded polystyrene by means of pyrolysis.

BACKGROUND OF THE INVENTION

Alongside the development of petrochemical industry, the application of synthetic polymers is becoming increasingly widespread, particularly a great quantity of synthetic polymeric substances are used as packing materials. At the same time, scraps of these materials are accumulated, among which the foam polystyrene occupies a significant proportion. The foam packing material causes a serious environmental pollution owing to the low density and the bulky volume. The other kind of scraps from polystyrene is also difficult to be processed and recycled. Burning and burying of the polystyrene scraps not only cause the resource waste, but also are not able to settle the pollution. In recent years a lot of research work has been carried out for recycling the discarded polymers. Attempts to obtain useful starting materials by means of pyrolysis and decomposition have been undertaken in many countries.

Yamamoto Makoto et al of Technology Institute, Waseda University in Japan, adopted distillation reactors to pyrolyze polystyrene (average molecular weight 99,000) at the temperature of 270° C., obtaining a liquid pyrolysis product containing 20% of styrene. JP74129772 disclosed a process of pyrolyzing polystyrene, which, using a pyrolysis tube 3 mm in diameter, involves pyrolysis of 16.6% solution of polystyrene in methylnaphthalene or tetralin at the temperature of 300° C. with the pyrolysis time of 506 sec. The recovery rate of styrene is 65.5%, and the solvent (s) could be repeatedly used. JP49099326 revealed a continuous method of preparing styrene through the pyrolysis of polystyrene. This method involves the introduction of overheated steam into a pyrolysis reactor containing a solution of polystyrene in benzene in the presence of copper powder as a catalyst at the temperature of 300° C. The recovery rate of styrene is 58.3%. The disadvantage of the methods described above consists in a requirement of a large quantity of aromatic compounds as solvent (s) for dissolution of polystyrene, which are costly and hard to be realized on an industrial scale. Another disadvantage of the methods described above is the low recovery rate of styrene monomer.

SUMMARY OF THE INVENTION

A method for retrieving styrene monomer from discarded polystyrene scarp through pyrolytic reduction is provided, in which an alloy additive is charged on the bottom of a pyrolyzer, a catalyst of metal oxide is used, when the pyrolyzer is heated to the temperature of 250° C., the discarded polystyrene granules 3-5 mm in diameter is continuously fed into the pyrolyzer at a rate of 0.15-0.20 kg per minute, when the temperature of the pyrolyzer reacher 350° C., gas is introduced at a flow rate of 1-2 1/kg.hr, under the temperature of 450°-500° C. the pyrolysis reaction is carried out with simultaneous feeding and distillation under a reduced pressure.

The object of the present invention is to provide a method for direct pyrolysis of polystyrene without using any solvent, which is easy to be carried out on a large scale commercially, and avoids the disadvantages of pyrolytic reduction described above.

The further object of the invention is to provide a method for increasing the recovery rate of styrene in the pyrolysis of polystyrene.

THE DETAILED DISCRIPTION OF THE INVENTION

The pyrolysis method of the present invention comprises the following steps: discarded polystyrene, for example, foam polystyrene or other polystyrene plastic is used as starting materials. Foam polystyrene, if used, should be processed in a roller mill before pyrolysis.

Firstly, clean foam polystyrene is processed in a rolling apparatus, the temperature of which is kept at 140° C. Removing foams from the foam polystyrene, the defoamed polystyrene is crushed in a crusher into granules 3-5 mm in diameter. Other kind of polystyrene plastics is also crushed into granules 3-5 mm in diameter.

To the bottom of a pyrolyzer are put granular lead-zinc (2:1), or lead-antimony (2:1), or tin-zinc alloys, and then put a catalyst metal oxides, for example zinc oxide, or alumina, or copper oxide. The pyrolyzer is closed and, then, heated. When the temperature of pyrolyzer reaches 250° C., the propeller feeding neck. which is located on the top of pyrolyzer, is switched on, discarded polystyrene granules (3-5 mm in diameter) being continuously introduced into the pyrolyzer at a constant speed till the whole polystyrene is added. As soon as polystyrene is fed into the pyrolyzer, the pyrolysis takes place. When the temperature reaches 350° C., nitrogen or carbon dioxide or overheated steam is gently passed through the pyrolyzer at the rate of 1.5-2.0 1 per hour and kilogram of polystyrene (1.5-2.0 1/kg.hr). If the reaction temperature no longer rises, the gas introduction should be stopped. About an hour later the temperature rises to 450° C. and should be kept in a range of 450°-500° C. till the reaction is complete. During feeding polystyrene the pyrolyzer is arranged for distillation under the reduced pressure of 0.013-0.20 MPa. Passing through a tube filled with porcelain rings absorbing a saturated solution of phenothiazine as a polymerization retarder, the distillate is led to a cooling tank to liquify at the temperature of $-5°-5°$ C. When the distillate output amounts to 85-90% of the total feed stock, the pyrolysis reaction is believed to be complete, and a normal pressure is restored. The outlet valve of the pyrolyzer is opened to discharge the formed asphalt, carbides, etc. The next operation could be performed after naturally cooling the pyrolyzer to the temperature below 200° C. According to the invention the distillate output amounts to 90% of the total feed stock (in weight). The liquid distillate consists of styrene monomer (70-75%), styrene dimer and trimer as well as ethylbenzene (15-20%), etc; the solid product contains asphalt and carbides (10%).

Polystyrene belongs to a family of high-molecular hydrocarbons with a low thermometric conductivity and high linear expansion coefficient. At the temperature above 80° C. it turns to a elastomer. Alloy additives, preferably lead-zinc alloy (2:1), are added into pyrolyzer in order for the pyrolyzed polystyrene to be homogeneously heated, to avoid being partially overheated, and to elevate the reaction temperature. Two hundred parts (by weight) of alloy additives are added for one hundred parts (by weight) of polystyrene. The additives can be repeatedly used because of no loss during the reaction.

The products of pyrolyzing polystyrene vary with reaction conditions, analytical data indicate that using silica/alumina (containing 21% of alumina) as catalysts and keeping the pyrolysis temperature of 270° C. the liquid products consist of benzene (35-53%), isopropylbenzene (15%), ethylbenzene (10%), and a high-boiling-point fraction (20-40%). Using metal oxides, the catalyst, provided in the invention, for example, zinc oxide, or alumina, or copper oxide, the recovery rate of styrene amounts to 70-75% under the reaction condition described above. The preferred catalyst is zinc oxide. The use level of catalyst is 0.02-0.05 part based on 100 parts of polystyrene by weight.

During the pyrolysis a constant flow of nitrogen or carbon dioxide or overheated steam is passed through the pyrolyzer in order to avoid producing a great quantity of low molecular by-products owing to the overheating decomposition of polystyrene, and to control the reaction rate. The gas flow rate should be maintained at 1-2 l/kg.hr.

This invention provides a simple and convenient method for retrieval of styrene monomer from pyrolyzing discarded polystyrene. The method is easy to be performed, and, in particular, the high recovery rate adapts to treat the discarded polystyrene on a large scale. This invention, therefore, provides an effective procedure either for solving the environmental pollution caused by discarded polystyrene or for retrieving polystyrene.

EXAMPLE 1

To the bottom of a pyrolyzer was put 200 kg of lead-zinc alloy (2:1) granules, and then added 0.04 kg of alumina catalyst. The pyrolyzer was closed and heated. At the temperature of 250° C. a propeller feeder installed on the top of the pyrolyzer was switched on. The granular polystyrene scarp 3-5 mm in diameter was continuously fed into the pyrolyzer through the feed inlet at a rate of 0.15 kg per minute. When the temperature reaches 350° C. nitrogen gas was gently introduced at a flow rate of 1 l/kg, hr. If the pyrolysis temperature no longer rose, nitrogen inlet should be stopped. The temperature was kept in the range of 450°-500° C. during the whole period of reaction. At the same time a reduced pressure distillation was performed. Under the pressure of 0.013-0.02 MPa a liquid was continuously distilled out. The operation was carried out at a feed rate of 0.15 kg per minute, till all the polystyrene was added. Passing through a tube filled with procelain rings absorbing a saturated solution of phenothiazine as a polymerization retarder, the distillate was led to a cooling tank to be liquefied at the temperature of −5°-5° C. When the distillate output amounts to 85-90% of the total feed stock, the pyrolysis reaction was believed to be complete, and the atmospheric pressure was restored. The outlet valve of the pyrolyzer was switched on to discharge the formed asphalt, carbides, etc. Yield: 144-150 kg of styrene monomer, 30-36 kg of styrene dimer and trimer as well as ethylbenzene, and about 20 kg of asphalt, carbides,etc.

EXAMPLE 2

To the bottom of a pyrolyzer was put 150 kg of lead-zinc alloy (2:1) granules, and then added 0.045 kg of zinc oxide catalyst. The pyrolyzer was closed and heated. At the temperature of 250° C. the propeller feeder installed on the top of the pyrolyzer was switched on. The granular polystyrene scarp was continuously fed into the pyrolyzer through the feed inlet at a rate of 0.20 kg per minute. When the temperature reached 350° C., carbon dioxide was gently introduced at a flow rate of 2 l/kg.hr. In a similar manner to example 1, 108-112 kg of styrene monomer, 22-27 kg of styrene dimer and trimer and ethylbenzene, and about 15 kg of asphalt and carbides etc. were obtained.

EXAMPLE 3

To the bottom of a pyrolyzer was put 200 kg of tin-zinc alloy (1.5:1) granules, and then added 0.1 kg of cooper oxide catalyst. The pyrolyzer was closed and heated. At the temperature of 250° C. the propeller feeder installed on the top of the pyrolyzer was switched on. The granular polystyrene scarp was continuously fed into the pyrolyzer through the feed inlet at a rate of 0.20 kg per minute. When the temperature reached 350° C., overheated steam was gently introduced at a flow rate of 1.5 l/kg.hr. In a similar manner to Example 1, 140-148 kg of styrene monomer, 32-40 kg of styrene dimer and trimer and ethylbenzene, and about 20 kg of asphalt and carbides were obtained.

We claim:

1. A method for recovering styrene monomer from polystyrene scarp material by means of pyrolytic reduction, comprising the steps of charging an alloy additive and a metal oxide catalyst selected from zinc oxide, alumina and copper oxide to a pyrolyzer, continuously feeding scrap polystyrene granules in size of 3-5 mm in diameter to the pyrolyzer at a rate of 0.15-0.20 kg per minute as the temperature in the pyrolyzer is heated to 250° C., introducing a gas into the pyrolyzer at a flow rate of 1-2 l/kg.hr as the temperature in the pyrolyzer reaches 350° C. carrying out the pyrolysis reaction at a temperature of 450°-500° C. with simultaneous feeding and distillation under reduced pressure.

2. A method according to claim 1, wherein said metal oxide is zinc oxide.

3. A method according to claim 1, wherein said metal oxide is used in an amount of 0.02-0.05 part based on 100 parts of polystyrene by weight.

4. A method according to claim 1, wherein said alloy additive is selected from the group consisting of lead-zinc alloy (2:1), lead-antimony alloy (2:1), and tin-zinc alloy (1.5:1).

5. A method according to claim 1, wherein said alloy additive is lead-zinc alloy (2:1).

6. A method according to claim 1, wherein said alloy additive is used in an amount of 200 parts based on 100 parts of polystyrene by weight.

7. A method according to claim 1, wherein said gas is selected from the group consisting of nitrogen, carbon dioxide and overheated steam.

8. A method according to claim 1, wherein said reduced pressure in the distillation is 0.013-0.20 MPa.

* * * * *